United States Patent [19]

Philpot, Jr.

[11] 4,150,118

[45] Apr. 17, 1979

[54] SNAKE VENOM INHIBITOR

[76] Inventor: Van B. Philpot, Jr., Philpot Memorial Laboratory, P.O. Box 312, Houston, Miss. 38851

[21] Appl. No.: 909,486

[22] Filed: May 25, 1978

[51] Int. Cl.² ..................... A61K 35/54; A61K 37/00
[52] U.S. Cl. ..................................... 424/105; 424/177
[58] Field of Search ................................. 424/105, 177

[56]  References Cited
PUBLICATIONS

Chem. Abst. 9th Coll. Index vol. 76–85 (1972–1976) p. 1105GS.

*Primary Examiner*—Sam Rosen
*Attorney, Agent, or Firm*—Cushman, Darby & Cushman

[57]  ABSTRACT

A snake venom antiprotease is isolated from the albumin fraction of the eggs of snakes, such as the Bushmaster, and used to treat mammals against the effects of snake venom according to the disclosed invention.

4 Claims, 1 Drawing Figure

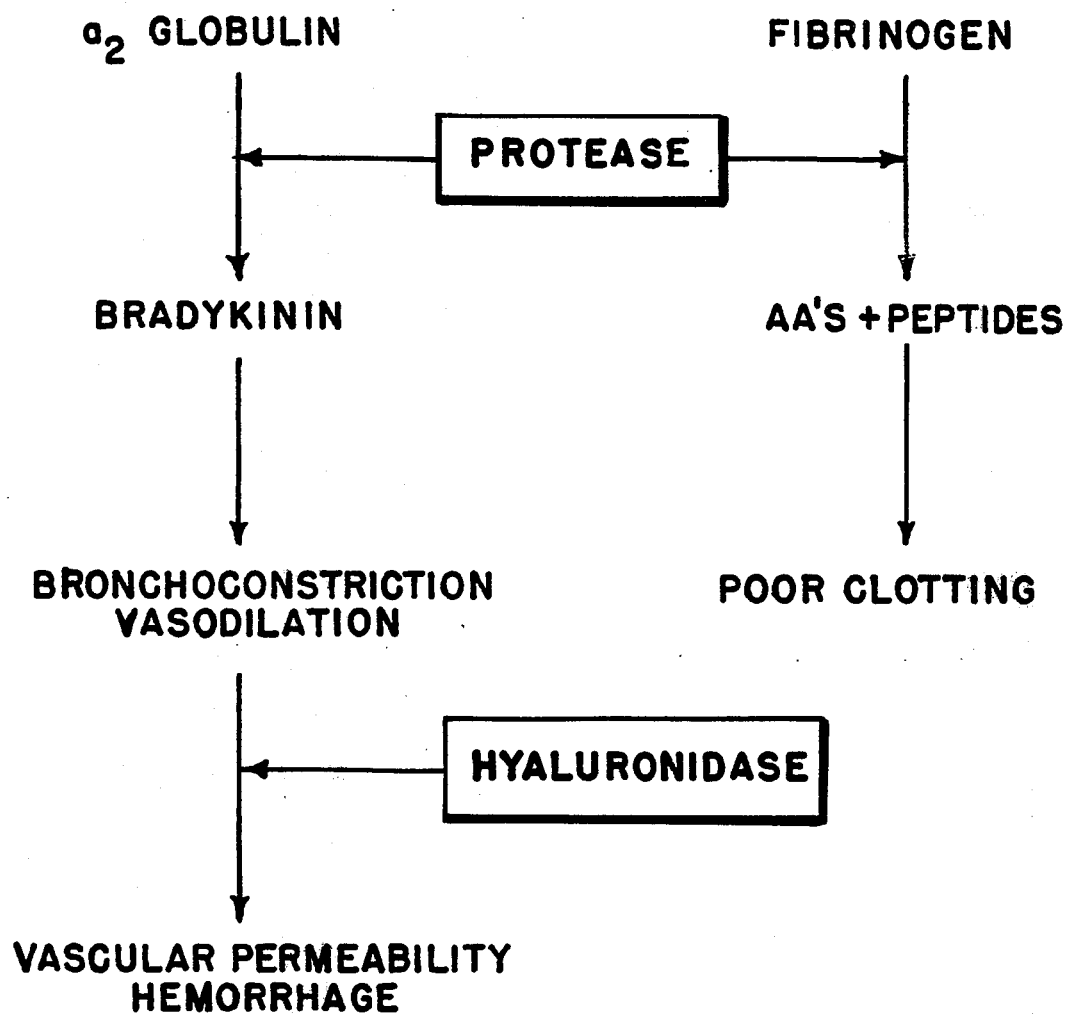

SNAKE VENOM INHIBITOR

BACKGROUND OF THE INVENTION

The pharmacological action of snake venom is one of the most complex phenomena is nature. In the past 20 years many unusual chemical constituents of venoms have been isolated and their physiological properties have been investigated.

The mortality rate from snake bites in the temperature and tropical zones of the world is in the neighborhood of 25,000 to 30,000 per year. Treatment of snake bites is a difficult problem which requires very special skills. Research is continuing on the production of improved as well as new methods for neutralizing the toxins of the snake venoms.

It is now well established that venomous snakes are not susceptable to large amounts of their own or closely related venoms. This observation led to the inquiry as to whether any protection was afforded by fractions of snake blood or snake plasma against the actions of the venom.

One of the most prominent pathologic changes produced by vipers and pit viper snake venoms is hemorrhage. It was proposed by Philpot and Deutsch, (Inhibition and Activation of Venom Proteases, Biochimica et Biophysica Acta, Vol. 29, pp. 524–530, 1956) that the hemorrhage was in part due to the presence of unique and powerful proteolytic enzymes in the venoms.

Deutsch and Dinitz (Journal of Biological Chemistry, Vol. 216 p. 17, 1955) demonstrated that the proteolytic activities of fifteen crotalid venoms of the genera *Crotalus* and *Bothrops* all were capable of liberating bradykinin from a serum globulin fraction and that all venoms digested fibrinogen far more rapidly than fibrin.

A simplified mechanism of crotalid venoms leading to hemorrhage and death can be illustrated in the attached FIGURE.

In this scheme it will be observed that the venom protease, shown schematically in the upper block, has at least two actions. The arrow pointing to the right indicates that plasma fibrinogen is fragmented resulting in poor clotting. The action of protease as shown with the arrow pointing to the left is liberation of bradykinin from a plasma globulin. Drastic elevation of bradykinin levels results in broncho-constriction and vasodilation. A second powerful hydrolytic enzyme in the crotalid venom is hyaluronidase shown in the lower block. This enzyme depolymerizes the mucopolysaccharides which hold the vascular cells together, thereby making the capillary bed permeable and resulting in hemorrhage. The consequence of generalized and extensive bleeding is death due to hypovolemic shock.

The prevention of hemorrhage and neutralization of the lethal effects of pit viper venoms by certain snake sera was demonstrated by Philpot and R. G. Smith as far back as 1950. (Proc. Soc. Exptl. Biol. Med., Vol. 74, p. 521, 1950)

Further work by Philpot and others has shown that a protein fraction is present in the sera of snakes belonging to the genus *Crotalidae* and *Colubridae* which protects mice from the lethal effect of $5 \times LD_{50}$ of crotalid venoms injected intra-peritoneally. Fractionation of the sera by ammonium sulfate precipitation and molecular sieving on Sephadex indicated that the neutralizing components of snake sera are contained in proteins of the molecular weight in the range of 70,000 to 90,000 Daltons. See U.S. Pat. No. 4,012,502 issued Mar. 15, 1977, the disclosure of which is hereby incorporated by reference. The most pronounced effect of the purified serum proteins there described was the ability to inhibit venom protease activity.

Although the venom protease resembles trypsin in its action, it is not inhibited by known trypsin inhibitors or by Trasylol, a known kallekrein inhibitor.

The inhibition of the venom protease by snake serum proteins is probably a deliberate event of nature which provides the snake with a self-protective mechanism, which is analogous to the trypsin-antitrypsin protective mechanism in mammals.

DETAILED DESCRIPTION OF THE INVENTION

I have found and now disclose the presence of a antiprotease in the albumin fraction of the snake egg of the South American pit viper, the Bushmaster (*Lachesis mutus*). This antiprotease may be similar to the "Antitrypsin" mechanism of mammals. The presence of the egg-antiprotease is believed to constitute a phylogenetic advantage which protects the snake embryo against its own venom.

For purposes of explanation the following example is given.

EXAMPLE

A solution of egg protein contain 6.5 grams percent protein was obtained from eggs of the Bushmaster snake (*Lachesis mutus*). To the egg protein (4 parts by volume) an aqueous saturated solution of sodium sulfate (6 parts by volume) was added. Proteins present in the egg source were precipitated and centrifuged down leaving a supernatant liquid. The pH of the supernatant liquid was adjusted to a pH of 4.8 with sulfuric acid (0.5N). To the supernatant an additional amount of saturated sodium sulfate was added until the first opalesence appeared. The thus treated solution was stirred overnight at ambient temperature, centrifuged the next morning and the solids separated then dialyzed against a phosphate buffered saline solution. The resulting albumin fraction was investigated for inhibitory activity against snake venom.

The protease activity of the bushmaster venom was determined in the presence of various snake egg proteins as shown in the following Table I.

TABLE I

| | Inhibition of Protease Activity in Bushmaster Venom | |
|---|---|---|
| Fraction | Mg Protein | Percent Inhibition |
| Chicken Egg (Crude) | 1.20 | 0 |
| Chicken Egg Globulin | 1.20 | 0 |
| Chicken Egg Albumin | 1.20 | 0 |
| Bushmaster Egg (Crude) | 1.30 | 44 |
| Bushmaster Egg Globulin | 0.54 | 0 |
| Bushmaster Egg Albumin | 0.17 | 25 |
| Bushmaster Egg Albumin | 0.34 | 60 |

It will be observed that globulin and albumin of the chicken egg have no apparent inhibitory activity. Egg proteins of the bushmaster, however, have significant inhibiting activity. Protease inhibition appears to reside in the albumin fraction, and there is no activity observed in connection with the egg globulins.

Next inhibition of protease activity was tested in water moccasin venom. It was observed that the bushmaster egg albumin fraction was capable of inhibiting the venom protease of a related pit viper venom.

The protease activity and its inhibition were tested by two different procedures: (a) the gelatin film technique, and (b) the azocoll assay system according to Moore.

Conclusive proof of neutralization of the bushmaster venom by bushmaster egg proteins was obtained in mortality experiments according to the following procedure.

The toxicity of the venoms was determined by intraperitoneal injection into white mice of the Swiss strain weighing 18 to 22 gms. The $LD_{50}$ for bushmaster venom was found to be 12 μg venom per gram of mouse. The venom and the egg proteins were mixed before inoculation. The amount of venom used for the mortality experiments was set at $3 \times LD_{50}$. Control mice were injected with only venom or egg proteins. The mice were observed for two days and dead mice were examined for evidence of internal bleeding.

TABLE II

Neutralization of Bushmaster Venom
By Bushmaster Egg Proteins
Venom Dose = $3 \times LD_{50}$

| Conditions | Mg Protein Per Gram | Percent Survival |
|---|---|---|
| Venom Control | — | 0 |
| V + Bush. Egg Glob. | 0.6 | 0 |
| V + Bush. Egg Alb. | 0.5 | 80 |
| Bush. Glob. Contr. | 0.6 | 100 |
| Bush. Alb. Contr. | 0.5 | 100 |
| V + Chick. Egg Glob. | 0.6 | 0 |

TABLE II-continued

Neutralization of Bushmaster Venom
By Bushmaster Egg Proteins
Venom Dose = $3 \times LD_{50}$

| Conditions | Mg Protein Per Gram | Percent Survival |
|---|---|---|
| V + Chick. Egg Alb. | 0.5 | 0 |

The results of these experiments are reported in Table II, above, and show that the venom neutralizing factor in bushmaster egg proteins resides in the albumin fraction, the same fraction which also contained the anti-protease factor. Chicken egg proteins have no protective effect.

I claim:

1. A method for protecting a mammal againsts the protease effects of snake venom comprising administering to said mammal a protease inhibiting amount of a selection albumin fraction isolated from the eggs of at least one snake.

2. The method of claim 1 wherein said snake is the Bushmaster (*Lachesis mutus*).

3. A process for separating and isolating an antiprotease effective protein fraction from the eggs of venomous snakes including the steps of:
   a. isolating albumin from the eggs of a venomous snake;
   b. treating said albumin with a precipitating agent causing a portion of the proteins contained therein to be precipitated;
   c. separating and discarding the precipitate from the supernatant liquid;
   d. subjecting the supernatant of step (c) to dialysis and isolating the anti-protease effective fraction therefrom.

4. The product produced by the process of claim 3.

* * * * *